US012708648B1

(12) United States Patent
Klitzke et al.

(10) Patent No.: US 12,708,648 B1
(45) Date of Patent: Aug. 18, 2026

(54) BIRTH TISSUE COMPOSITIONS AND METHODS OF PREPARATION

(71) Applicant: Triad Life Sciences, Inc., Memphis, TN (US)

(72) Inventors: Kurt Klitzke, Memphis, TN (US); Jon G. Hargis, Memphis, TN (US)

(73) Assignee: CONVATEC, INC, Bridgewater, NJ (US)

( * ) Notice: Subject to any disclaimer, the term of this patent is extended or adjusted under 35 U.S.C. 154(b) by 467 days.

(21) Appl. No.: 17/412,700

(22) Filed: Aug. 26, 2021

Related U.S. Application Data

(63) Continuation of application No. 16/270,052, filed on Feb. 7, 2019, now abandoned.

(60) Provisional application No. 62/627,971, filed on Feb. 8, 2018.

(51) Int. Cl.
*A61K 38/00* (2006.01)
*A61K 9/14* (2006.01)
*A61K 35/50* (2015.01)
*A61K 38/39* (2006.01)
*A61P 17/02* (2006.01)
*A61K 48/00* (2006.01)

(52) U.S. Cl.
CPC ................ *A61K 35/50* (2013.01); *A61K 9/14* (2013.01); *A61K 38/39* (2013.01); *A61P 17/02* (2018.01)

(58) Field of Classification Search
CPC .......... A61K 35/50; A61K 38/39; A61P 17/02
See application file for complete search history.

(56) References Cited

U.S. PATENT DOCUMENTS 4,212,761 A * 7/1980 Ciaccio
4,647,283 A 3/1987 Carpentier et al.
5,756,678 A 5/1998 Shenoy
6,203,755 B1 3/2001 Odland
7,795,493 B2 9/2010 Phelps et al.
8,106,251 B2 1/2012 Ayares et al.
9,642,937 B2 5/2017 Zhao et al.
9,808,491 B2 11/2017 Tseng et al.
11,116,871 B2 9/2021 Daniel
2002/0160510 A1 10/2002 Hariri
2004/0048796 A1 3/2004 Hariri et al.
2007/0038298 A1 2/2007 Sulner
2013/0230561 A1 9/2013 Daniel
2015/0182664 A1 7/2015 Ayares et al.
2015/0250829 A1 9/2015 Daniel
2018/0126036 A1 5/2018 Early

FOREIGN PATENT DOCUMENTS

CN 107007885 A 8/2018
EP 0738106 B1 8/2001
WO WO 91/00334 * 1/1991
WO 2003030949 A1 4/2003
WO 2012141454 A2 10/2012
WO 2015017500 A1 2/2015
WO WO-2015168254 A1 * 11/2015 ............ A61L 27/34
WO 2017017474 A1 2/2017
WO 2017076782 A1 5/2017
WO WO-2017112934 A1 * 6/2017 ............ A61K 35/50
WO 2017140914 A1 8/2018

OTHER PUBLICATIONS

Furukawa, S., "A comparison of the histological structure of the placenta in experimental animals", J. Toxicol Pathol (2014), vol. 27, pp. 11-18.
Gupta et al., "Amnion and Chorion Membranes: Potential Stem Cell Reservoir with Wide Applications in Periodontics", 2015, International Journal of Biomaterials, vol. 2015, p. 1-9.
Agilent Technologies, "Safety Data Sheet: Phosphate Buffer Saline—PBS", 2015, https://www.agilent.com/cs/library/msds/SDS211_NAEnglish.pdf, [accessed: Sep. 22, 2020].
Brantley, J.N., et al.. "Use of placental membranes for the treatment of chronic diabetic foot ulcers", Adv. Wound Care (New Rochelle), (Sep. 1, 2015), vol. 4, No. 9, pp. 545-559.
Balestrini, J.L., et al., "Production of decellularized porcine lung scaffolds for use in tissue engineering", Integr. Biol. (Dec. 2015), vol. 7, No. 12, pp. 1598-1610.
Gilpin, A., et al., "Decellularization strategies for regenerative medicine: from processing techniques to applications", Biomed Res. Int. (2017), vol. 2017, Article ID: 9831534, 13 pages.
Deshmukh, S.N., et al., "Enigmatic insight into collagen", J. Oral Maxillofac. Pathol. (May-Aug. 2016), vol. 20, No. 2, pp. 276-283.
Kosswig, K., "Surfactants", Ullman's Encycl. Ind. Chem. (2012), A25, 450.
Office Action from corresponding U.S. Appl. No. 16/270,052, dated Apr. 1, 2022.
Office Action from corresponding U.S. Appl. No. 16/284,351, dated Jul. 12, 2021.
Affidavit of Jon Hargis from U.S. Appl. No. 16/270,052, filed Dec. 15, 2021.

* cited by examiner

*Primary Examiner* — Quang Nguyen
(74) *Attorney, Agent, or Firm* — Barnes & Thornburg LLP

(57) ABSTRACT

Methods of processing a mammalian placental tissue to form birth tissue compositions are provided. The birth tissue compositions may be a membrane-based construct or a powder formulation. Methods of treating a wound are also provided.

18 Claims, No Drawings

BIRTH TISSUE COMPOSITIONS AND METHODS OF PREPARATION

CROSS-REFERENCE TO RELATED APPLICATIONS

The present application is a continuation of U.S. Ser. No. 16/270,052 filed Feb. 7, 2019 which claims priority to U.S. Provisional Application No. 62/627,971 filed Feb. 8, 2018, the contents of which are each incorporated herein in their entirety.

BACKGROUND OF THE INVENTION

Human placental tissue has been utilized for various purposes over the past century for regenerative medicine purposes. There remains a need, however, for regenerative products derived from alternative sources.

SUMMARY OF THE INVENTION

The present invention is generally directed to birth tissue compositions and processes for producing such birth tissue compositions. The birth tissue compositions as disclosed herein exhibit various regenerative properties. The membrane-based birth tissue compositions as provided herein can be cut into a variety of sizes as may be desirable for a particular application. The birth tissue compositions may also be placed on other areas of the body that have sustained damage but have not been subjected to surgical intervention.

According to one aspect, a birth tissue composition is provided. According to one embodiment, the birth tissue composition includes at least one dehydrated porcine placental membrane. According to one embodiment, the composition is formulated as a membrane-based construct. According to one embodiment, the at least one dehydrated porcine placental membrane is at least one placental membrane, at least one amnion membrane, at least one chorion membrane or any combination thereof. According to one embodiment, the composition is formulated as a powder.

According to another aspect, a birth tissue composition is provided. According to one embodiment, the birth tissue composition includes a dehydrated mammalian placental membrane treated with a bioburden reduction step, a detergent rinse step, and a viral inactivation step. According to one embodiment, the dehydrated mammalian placental membrane exhibits a pH of between about 6.8 and about 7.2. According to one embodiment, the composition is formulated as a powder.

According to another aspect, a birth tissue composition is provided. According to one embodiment, the birth tissue composition includes a dehydrated mammalian placental membrane treated with a sodium chloride solution, a detergent solution, a sodium hydroxide solution, and a buffer solution. According to one embodiment, the dehydrated mammalian placental membrane exhibits a pH of between about 6.8 and about 7.2. According to one embodiment, the composition is formulated as a powder.

According to another aspect, a method of preparing a membrane for a birth tissue composition is provided. The method includes the steps of:

a) introducing from about 5 mL to about 25 mL of 3M sodium chloride solution per gram of placental membrane to the placental membrane;
b) decanting the 3M sodium chloride;
c) rinsing the sodium chloride from the placental membrane with water;

d) introducing from about 5 mL to about 25 mL of a detergent solution per gram of placental membrane to the placental membrane;
e) decanting the detergent solution;
f) rinsing the detergent solution from the placental membrane with water;
g) introducing from about 5 mL to about 15 mL of 0.1M to 1.0M sodium hydroxide per gram of placental membrane;
h) rinsing the sodium hydroxide from the placental membrane with water;
i) introducing from about 5 mL to about 50 mL of buffer solution per gram of placental membrane to the placental membrane;
j) decanting the buffer solution;
k) measuring the pH of the placental membrane;
l) repeating steps i), j) and k) until the pH of the placental membrane is between about 6.8 and about 7.2;
m) rinsing the buffer solution from the placental membrane with water; and
n) dehydrating the placental membrane to form a birth tissue composition.

According to one embodiment, the detergent solution includes at least one anionic detergent and at least one protease enzyme. According to one embodiment, the detergent solution includes sodium linear alkylaryl sulfonate, phosphates, carbonates and at least one protease enzyme. According to one embodiment, the female mammal is a pig that is not genetically modified to halt or reduce expression of a functional alpha-1,3 galactosyltransferase gene. According to one embodiment, the method further includes the steps of:

o) cutting the placental membrane to a predetermined size;
p) packaging the placental membrane; and
q) terminally sterilizing the packaged placental membrane.

According to one embodiment, the step of dehydrating the placental membrane is carried out by treating the placental membrane with an alcohol. According to one embodiment, the alcohol is 200 proof ethanol. According to one embodiment, the step of dehydrating the placental membrane is carried out by placing the placental membrane on a drying table for sufficient time to allow any water present to evaporate.

According to another aspect, a birth tissue composition is provided that is produced by any of the aforementioned methods.

According to another aspect, a method of treating a wound is provided that includes the steps of providing a birth tissue composition as provided herein and placing the birth tissue composition on or around a wound. According to one embodiment, the wound is an ulcer, abrasion or burn.

According to another aspect, a method of preparing a membrane for a birth tissue powder composition is provided. The method includes the steps of:

a) introducing from about 5 mL to about 25 mL of 3M sodium chloride solution per gram of placental membrane to the placental membrane;
b) decanting the 3M sodium chloride;
c) rinsing the sodium chloride from the placental membrane with water;
d) introducing from about 5 mL to about 25 mL of a detergent solution per gram of placental membrane to the placental membrane;
e) decanting the detergent solution;

f) rinsing the detergent solution from the placental membrane with water;

g) introducing from about 5 mL to about 15 mL of 0.1M to 1.0M sodium hydroxide per gram of placental membrane;

h) rinsing the sodium hydroxide from the placental membrane with water;

i) introducing from about 5 mL to about 50 mL of buffer solution per gram of placental membrane to the placental membrane;

j) decanting the buffer solution;

k) measuring the pH of the placental membrane;

l) repeating steps i), j) and k) until the pH of the placental membrane is between about 6.8 and about 7.2;

m) rinsing the buffer solution from the placental membrane with water;

n) dehydrating the placental membrane to form a birth tissue composition; and o) milling or grinding the placental membrane to a powder form.

According to one embodiment, the method further includes the steps of:

p) packaging the birth tissue powder composition;

q) lyophilizing the packaged birth tissue powder composition to remove residual moisture; and r) terminally sterilizing the packaged birth tissue powder composition.

According to one embodiment, the female mammal is a pig that is not genetically modified to halt or reduce expression of a functional alpha-1,3 galactosyltransferase gene.

According to another aspect, a powdered birth tissue composition is provided that is produced by any of the aforementioned methods.

According to another aspect, a method of treating a wound is provided that includes the steps of providing a birth tissue powder composition as provided herein and placing the birth tissue powder composition on or around a wound. According to one embodiment, the wound is an ulcer, abrasion or burn.

According to another aspect, a dehydrated porcine placental membrane including collagen I, collagen IV, elastin, laminin, fibronectin and hyaluronic acid is provided. According to one embodiment, the dehydrated porcine placental membrane including collagen I, collagen IV, elastin, laminin, fibronectin and hyaluronic acid has a pH of between about 6.8 and about 7.2

DETAILED DESCRIPTION OF THE INVENTION

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the present disclosure may be embodied in many different forms and should not be construed as limited to the embodiments set forth herein; rather, these embodiments are provided so that this disclosure will satisfy applicable legal requirements.

As used in the specification, and in the appended claims, the singular forms "a", "an", "the", include plural referents unless the context clearly dictates otherwise. As used in the specification, and in the appended claims, the words "optional" or "optionally" mean that the subsequently described event or circumstance can or cannot occur.

The present disclosure provides birth tissue composition that is prepared from mammalian birth tissue. The present disclosure particularly provides a birth tissue composition that is prepared from pig birth tissue.

As used herein, the term "birth tissue" includes, but is not limited to, elements of a mammalian placental organ such as, for example, the umbilical cord, amniotic fluid and placental membrane (amnion membrane and chorion membrane).

As used herein, the term "placental membrane" refers to the full, intact placental membrane including the amnion and chorion layers that are obtained from a mammal such as, for example, a pig or human.

As used herein, the terms "pig" and "porcine" may be used interchangeably.

As used to herein, the terms "birth tissue composition" and "birth tissue powder composition" refer to a construct that is applied onto or around an injured area of a mammalian body.

As used herein, the term "wound" refers to an injured area of the body.

As used herein, the term "membrane" refers to at least one placental membrane, at least one amnion membrane, at least one chorion membrane or any combination thereof. The membranes as referred to herein may be obtained from a mammal such as, for example, a pig or human.

The birth tissue compositions as provided herein may aid in the healing cascade or healing process of a mammalian wound. The birth tissue compositions are fully resorbed by the mammal's body during the healing process. Methods for aseptically processing placental membrane to prepare birth tissue compositions are provided. According to one embodiment, the placental membranes remain intact in that the placental membranes retain the amnion and chorion membrane layers and any intermediate layers. According to one embodiment, the placental membrane is processed in a manner such that all native layers are retained except for the Wharton's Jelly.

The birth tissue compositions may be used for a variety of regenerative medicine purposes. According to one embodiment, the regenerative medical use is for treatment of wounds. Other suitable uses include inflammation reduction (anti-inflammatory); pain reduction; anti-adhesion; skin wrinkle reduction, skin resurfacing, skin rejuvenation, and other cosmetic purposes; nerve repair; soft tissue repair; bone repair; joint pain treatment; dura preservation; ocular defect treatment and other similar regenerative uses. Exemplary wounds that may be treated with the birth tissue compositions as provided herein include partial and full thickness wounds; pressure ulcers; venous ulcers; diabetic ulcers; chronic vascular ulcers; tunneled/undermined wounds; surgical wounds (e.g., donor sites/grafts, post-Mohs surgery, post-laser surgery, podiatric, wound dehiscence); trauma wounds (e.g., abrasions, lacerations, second degree burns, skin tears); and draining wounds. The birth tissue compositions may also be utilized on any wound arising on or around a soft tissue, nerve, organ, vascular tissue, muscle, spinal cord, bone, oral cavity, ocular surface, or a combination thereof.

The birth tissue compositions as provided herein may be formulated as a membrane-based construct. According to one embodiment, the birth tissue composition includes one or more layers of porcine placental membrane. The birth tissue composition as provided herein may also be formulated as a powder, gel, liquid or spray.

According to one embodiment, when formulated as a membrane-based construct, the membrane may be treated to provide for the delivery of a variety of antibiotics, anti-inflammatory agents, growth factors and/or other specialized proteins or small molecules. In addition, the membrane may be combined with a substrate (sterile gauze, sterile polymer material or other tissue or biomaterial) to increase the strength of the birth tissue composition dressing for sutures or to increase the longevity of an implant. A birth tissue composition as described herein may be produced by processing mammalian birth tissue according to any or all of the steps provided herein as applied to birth tissue. According to a particular embodiment, a birth tissue composition as described herein may be produced by processing pig or human birth tissue according to the steps provided herein.

According to one embodiment, a method of preparing a birth tissue composition is provided. The method includes the step of collecting the placental organ, including the umbilical cord, placental membrane (amnion and chorion membrane), and amniotic fluid from a female mammal. According to one embodiment, the method includes the step of collecting the placental organ, including the umbilical cord, placental membrane (amnion and chorion membrane), and amniotic fluid from a female pig. According to one embodiment, the female pig is not genetically modified to halt or reduce expression of the functional alpha-1,3 galactosyltransferase gene. According to one embodiment, the placental membrane includes the umbilical cord attached. Potential birth tissue donors are screened and tested to exclude any donors that may present a health risk. According to one embodiment, birth tissue is recovered from a full-term delivery of one or more offspring such as an infant or piglet(s). According to one embodiment, the method further includes the step of placing the placental organ, including the umbilical cord and placental membrane (amnion and chorion membrane), in a transport container. According to one embodiment, the method further includes the step of placing the placental organ, including the umbilical cord and placental membrane (amnion and chorion membrane), in a transport container containing transport solution.

According to one embodiment, the method further includes the step of rinsing the placental organ, including the umbilical cord and placental membrane (amnion and chorion membrane) with water. According to a particular embodiment, the water is sterile water. According to a particular embodiment, the water is type 1 water. According to one embodiment, the method further includes the step of removing a substantial portion of any residual moisture present on the umbilical cord and placental membrane.

According to one embodiment, the method further includes the step of freezing the umbilical cord and placental membrane. According to one embodiment, the umbilical cord and placental membrane may be kept frozen until further processing is needed. According to one embodiment, the method further includes the step of removing the frozen, bagged umbilical cord and placental membrane from the freezer and thawing in a refrigerator for about three (3) to five (5) days. According to one embodiment, the method further includes the step of thawing the umbilical cord and placental membrane at ambient temperature. According to one embodiment, the method optionally includes the step of placing any retained, frozen amniotic fluid in a container.

According to one embodiment, the method includes rinsing the umbilical cord and placental membrane with water. According to a particular embodiment, the water is sterile water. According to one embodiment, the water is type 1 water. According to one embodiment, the method includes draining the umbilical cord and placental membrane. According to one embodiment, the method includes the step of opening any tube-shaped placental tissue so the placental membrane will lie flat onto a cutting surface. According to one embodiment, the method includes separating the placental membrane from the umbilical cord.

According to one embodiment, the method includes the step of dividing the placental membrane into pieces. According to one embodiment, a rotary cutter or other suitable cutter is used to cut the pieces. When formulated as a membrane-based construct, the birth tissue may be cut to various sizes, thickness, and shapes. The placental membrane pieces are preferably of sufficient size and shape to be applied onto or around a wound that is on or in a mammalian patient's body. The placental membrane thickness may vary depending on application, the type of membrane and the number of membrane layers.

According to one embodiment, the method includes the step of removing Wharton's jelly and excess fluids from the placental membrane to produce cleaned placental membrane. According to one embodiment, the method includes the step of weighing the cleaned placental membrane on a tared balance.

According to one embodiment, the method includes the step of treating the placental membrane with a bioburden reduction solution. According to a preferred embodiment, the bioburden reduction solution is sodium chloride. According to one embodiment, the method includes the step of adding from about 5 mL to about 25 mL of 3M sodium chloride solution per gram of placental membrane to the cleaned placental membrane. According to one embodiment, the method includes the step of adding about 20 mL of 3M sodium chloride solution per gram of placental membrane to the cleaned placental membrane. According to one embodiment, the method includes the step of immersing the placental membrane in the sodium chloride solution from about thirty minutes to about two hours. According to a preferred embodiment, the method includes the step of immersing the placental membrane in the sodium chloride solution for about one hour. According to one embodiment, the method includes the step of shaking the placental membrane in the sodium chloride solution from about thirty minutes to about two hours at about 50 RPM to about 100 RPM. According to a preferred embodiment, the method includes the step of shaking the placental membrane in the sodium chloride solution for about one hour at about 50 RPM to about 100 RPM. According to one embodiment, the placental membrane is shaken on an orbital shaker table.

According to one embodiment, the method includes the step of decanting the sodium chloride. According to one embodiment, the method includes the step of rinsing the placental membrane with water. According to a particular embodiment, the water is sterile water. According to a particular embodiment, the method includes the step of washing the placental membrane with about 20 mL of sterile water per gram of placental membrane. According to one embodiment, the water is type 1 water. According to one embodiment, the placental membrane is washed one time. According to one embodiment, the placental membrane is washed at least two times. According to one embodiment, the placental membrane is washed at least three times. According to one embodiment, the method includes the step of removing excess fluids.

According to one embodiment, the method includes the step of placing the placental membrane in from about 5 mL to about 25 mL of a detergent solution. According to a particular embodiment, the method includes the step of placing the placental membrane in about 20 ml of a detergent solution. According to a particular embodiment, the method includes the step of placing the placental membrane in about 20 mL of a detergent solution per gram of placental membrane. According to one embodiment, the detergent is present at a concentration of about 0.25% to about 3% w/v. According to one embodiment, the detergent is present at a concentration of about 1% w/v. According to a particular embodiment, the detergent solution includes at least one anionic detergent and at least one protease enzyme. According to one embodiment, the detergent solution includes sodium linear alkylaryl sulfonate, phosphates, carbonates and at least one protease enzyme. According to one embodiment, the detergent solution is commercially available under the trade name Tergazyme™. According to one embodiment, the detergent solution is a 1% Tergazyme™ solution. According to one embodiment, the method includes the step of immersing the placental membrane in the detergent solution for from about one hour to about three hours. According to a particular embodiment, the method includes the step of immersing the placental membrane in the detergent solution for about two hours. According to one embodiment, the method includes the step of shaking the placental membrane in the detergent solution for from about one hour to about three hours at about 50 RPM to about 100 RPM. According to one embodiment, the method includes the step of shaking the placental membrane in the detergent solution for about two hours at about 50 RPM to about 100 RPM. The shaking may be carried out on an orbital shaker.

According to one embodiment, the method includes the step of decanting the detergent solution. According to one embodiment, the method includes the step of washing the placental membrane with from about 5 mL to about 25 mL of water per gram of placental membrane. According to one embodiment, the method includes the step of washing the placental membrane with about 20 ml of water per gram of placental membrane. According to a particular embodiment, the water is sterile water. According to one embodiment, the water is type 1 water. According to one embodiment, the placental membrane is washed one time. According to one embodiment, the placental membrane is washed at least two times. According to one embodiment, the placental membrane is washed at least three times. According to one embodiment, the method includes the step of removing excess fluids.

According to one embodiment, the method includes the step of treating the placental membrane with a viral inactivation solution. According to a preferred embodiment, the viral inactivation solution is sodium hydroxide. According to one embodiment, the method includes the step of adding or introducing from about 5 mL to about 15 mL of about 0.1M to about 1.0M sodium hydroxide per gram of placental membrane. According to one embodiment, the method includes the step of adding or introducing from about 5 mL to about 15 mL of 0.25M sodium hydroxide per gram of placental membrane. According to one embodiment, the method includes the step of adding or introducing about 10 mL of 0.25M sodium hydroxide per gram of placental membrane. According to one embodiment, the method includes the step of immersing the placental membrane in the sodium hydroxide for about 15 minutes to about 45 minutes. According to one embodiment, the method includes the step of immersing the placental membrane in the sodium hydroxide for about 20 minutes. According to one embodiment, the method includes the step of shaking the placental membrane in the sodium hydroxide for about 15 minutes to about 45 minutes at about 50 RPM to about 100 RMP. According to one embodiment, the method includes the step of shaking the placental membrane in the sodium hydroxide for about 20 minutes at about 50 RPM to about 100 RPM. The shaking may be carried out on an orbital shaker. The sodium hydroxide may then be decanted. According to one embodiment, the steps of adding sodium hydroxide, shaking and decanting may be repeated as many times as necessary to inactivate any viruses present in the placental membrane to produce a placental membrane that is substantially void of viruses. According to one embodiment, the steps of adding sodium hydroxide, shaking and decanting may be repeated once. According to one embodiment, the steps of adding sodium hydroxide, shaking and decanting may be repeated twice.

According to one embodiment, the method includes the step of rinsing the placental membrane with water. According to a particular embodiment, the water is sterile water. According to a particular embodiment, the step of rinsing the placental membrane with sterile water is carried out for up to about 10 minutes. According to one embodiment, the water is type 1 water. According to one embodiment, the method includes the step of removing excess fluids.

According to one embodiment, the method includes the step of adding or introducing from about 5 mL to about 50 mL of buffer solution per gram of placental membrane. According to a particular embodiment, the method includes the step of adding or introducing about 20 mL of buffer solution per gram of placental membrane. According to one embodiment, the method includes the step of immersing the placental membrane in the buffer solution. According to one embodiment, the method includes the step of shaking the placental membrane in the buffer solution for about 5 minutes to about 45 minutes at about 50 RPM to about 100 RPM. According to one embodiment, the method includes the step of shaking the placental membrane in the buffer solution for about 20 minutes at about 50 RPM to about 100 RPM. The shaking may be carried out on an orbital shaker. The buffer solution may then be decanted. According to a preferred embodiment, the buffer solution is phosphate-buffered saline. According to one embodiment, the method includes the step of measuring the pH of the placental membrane after buffer solution treatment. According to one embodiment, the steps of adding buffer solution, shaking and decanting may be repeated until the pH of the placental membrane is between about 6.8 and about 7.2.

According to one embodiment, the method includes the step of rinsing the placental membrane with water. According to a particular embodiment, the water is sterile water. According to one embodiment, the water is type 1 water. According to one embodiment, the placental membrane is washed one time. According to one embodiment, the rinsing step is carried out multiple times. According to a one embodiment, the rinsing step is carried out at least twice. According to a one embodiment, the rinsing step is carried out at least three times. According to one embodiment, the method further includes the step of removing a substantial portion of any residual moisture present in the placental membrane.

According to one embodiment, the placental membrane may be dehydrated by any method known in the art, including, but not limited to, chemical dehydration (e.g., organic solvents), lyophilization, desiccation, oven dehydration and air drying. According to a preferred embodiment, the method includes the step of adding or introducing an alcohol to the placental membrane to cover the entire surface of the placental membrane (i.e., submerge the placental membrane). According to one embodiment, the method includes the step of adding or introducing from about 1 mL to about 10 mL of alcohol per gram of placental membrane. According to one embodiment, the method includes the step of adding or introducing about 5 mL of alcohol per gram of placental membrane. According to one embodiment, the placental membrane is fully submerged in the alcohol for from about one hour to about 24 hours. According to one embodiment, the placental membrane is not agitated while in contact with the alcohol. The alcohol may be any alcohol-safe and appropriate for contact with placental membrane. According to a particular embodiment, the alcohol is ethanol. According to another embodiment, the ethanol is from about 90%-100% ethanol. According to a particular embodiment, the ethanol is 200 proof (i.e., absolute ethanol). According to one embodiment, the method includes the step of decanting or draining the alcohol from the placental membrane.

According to one embodiment, the method includes the step of spreading the placental membrane onto a drying table (e.g., a Delrin drying table). According to one embodiment, the placental membrane may be blotted with a micro fiber wipe or similar. The placental membrane may be spread in a manner so as to fully dehydrate the placental membrane while ensuring no wrinkles or bubbles are present.

When preparing a membrane-based construct, the method includes the step of cutting the fully dehydrated placental membrane to a predetermined or desired size. According to one embodiment, the placental membrane is cut to size with a rotary cutter or other suitable instrument According to one embodiment, the cuts are made with a scalpel blade.

According to one embodiment, the method includes the step of placing the cut placental membrane in an inner packaging pouch or container and then sealing it. A sterilization indicator may be placed in a bottom portion of the inner pouch or container. According to one embodiment, an impulse sealer may be used to seal an inner package. According to one embodiment, the sealed inner package may then be placed into and sealed within an outer package.

According to one embodiment, the method includes the step of terminally sterilizing the packaged placental membrane. According to one embodiment, the method of terminal sterilization may be e-beam irradiation, gamma irradiation, peracetic acid treatment, vaporized peracetic acid (VPA) treatment, any combination thereof, or any other terminal sterilization method known in the art.

When preparing a powder-based composition, the placental membrane may be wet or dehydrated. According to one embodiment, the powder-based composition may be dehydrated by any method known in the art, including, but not limited to, chemical dehydration (e.g., organic solvents), lyophilization, desiccation, oven dehydration and air drying. In one embodiment, the method includes the step of cutting the placental membrane into a plurality of strips. According to one embodiment, the strips of placental membrane may then be placed into a mill and ground into a powder to form a birth tissue powder composition. According to one embodiment, the whole placental membrane or a portion thereof may be placed into a mill and ground into a powder to form a birth tissue powder composition. According to one embodiment, the birth tissue powder composition may then be placed into appropriate containers or vials at a desired concentration. According to one embodiment, the method of preparing a powder-based composition includes the step of lyophilizing the milled/ground powder-based composition within the vials to remove residual moisture. The vials containing the powder-based composition are then terminally sterilized. According to one embodiment, the method of terminal sterilization may be e-beam irradiation, gamma irradiation, peracetic acid treatment, vaporized peracetic acid (VPA) treatment, any combination thereof, or any other terminal sterilization method known in the art.

According to one embodiment, a dehydrated porcine placental membrane including one or more of collagen I, collagen IV, elastin, laminin, fibronectin and hyaluronic acid is provided. According to one embodiment, each of the one or more of collagen I, collagen IV, elastin, laminin, fibronectin and hyaluronic acid is present in the dehydrated porcine placental membrane in an amount that is different from a porcine placental membrane that is not processed according to one or more of the processing steps provided herein. According to one embodiment, collagen I is present in an amount of from about 0.001% w/w to about 99.9% w/w based on the total weight of the membrane. According to one embodiment, collagen IV is present in an amount of from about 0.001% w/w to about 99.9% w/w based on the total weight of the membrane. According to one embodiment, elastin is present in an amount of from about 0.001% w/w to about 99.9% w/w based on the total weight of the membrane. According to one embodiment, laminin is present in an amount of from about 0.001% w/w to about 99.9% w/w based on the total weight of the membrane. According to one embodiment, fibronectin is present in an amount of from about 0.001% w/w to about 99.9% w/w based on the total weight of the membrane. According to one embodiment, hyaluronic acid is present in an amount of from about 0.001% w/w to about 99.9% w/w based on the total weight of the membrane.

A method of treating a wound is also provided. According to one embodiment, the method includes the step of providing a birth tissue composition as provided herein. The birth tissue composition is then placed on or around a wound. The wound may be a burn, cut, abrasion, and ulcer. According to one embodiment, the wound may be a surgical site anywhere on a mammalian body. The birth tissue composition may be placed over a surgical site or held in place by a patient's musculature or skin. Sutures or staples may also be used to hold a membrane-based birth tissue composition in place. The birth tissue composition may be hydrated at the application site during treatment. The birth tissue composition can also be used to cover an implant or other device that may be placed on or within a mammalian body.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

EXAMPLE

Porcine placental membrane processed according to the methods as provided herein (i.e., steps a)-n) set forth herein). Particularly, porcine placental membrane was treated with a bioburden solution, treated with a detergent solution, treated with a viral inactivation solution and dehydrated according the methods as provided herein. The resulting dehydrated porcine placental membrane was analyzed to assess the presence of the following extracellular matrix components: collagen I, collagen IV, elastin, laminin, fibronectin, and hyaluronic acid (HA). An immunostaining procedure was carried out utilizing a primary antibody to detect the specific protein in the sample and then a secondary antibody that is labeled with a fluorophore to detect any bound primary antibody. Utilizing this methodology enabled improved detection of the primary antibodies since two or more secondary antibodies can detect a single primary antibody and thereby increase the fluorescent signal for imaging.

The following primary antibodies were used:

Rabbit Anti-Collagen I antibody (Cat #ab34710 Abcam, Cambridge, MA, USA).

Rabbit Anti-Collagen IV antibody (Cat #ab6586 Abcam, Cambridge, MA, USA)

Rabbit Anti-Elastin antibody (Cat #ab21610 Abcam, Cambridge, MA, USA)

Rabbit Anti-Laminin antibody (Cat #ab11575 Abcam, Cambridge, MA, USA)

Rabbit Anti-Fibronectin antibody (Cat #ab2413 Abcam, Cambridge, MA, USA)

Mouse Anti-Hyaluronic Acid antibody (Cat #CAU29210 Biomatik, Wilimgton, DE, USA)

The following secondary antibodies were used:

Anti-Rabbit 488 secondary antibody (provided by the Integrated Microscopy Center, The University of Memphis, Memphis, TN, USA).

Anti-Mouse 594 secondary antibody (provided by the Integrated Microscopy Center, The University of Memphis, Memphis, TN, USA).

One centimeter diameter samples were cut at random from ten sterile porcine placental membrane samples (approximately 2.5 cm diameter by <0.5 mm thick). Triplicate samples were evaluated for each matrix component. Samples were attached to cover slips (approximately 2 cm diameter) using phosphate buffered saline (PBS). The samples were allowed to dry at ambient conditions overnight. Samples were then were soaked in 1% NP-40 (a detergent used to increase permeability of biological specimen for staining procedures) for 5 minutes and then rinsed three times with approximately 1 ml of PBS. The primary antibodies for collagen I, collagen IV, elastin, laminin, fibronectin, and hyaluronic acid (HA) were diluted 1:20 in PBS. The samples were covered with 50 μl of the primary antibody dilutions and incubated overnight at 4° C. The next day, the samples were rinsed three times with approximately 1 ml PBS to remove unbound primary antibodies. The secondary antibodies were diluted 1:50 in PBS and the samples were covered with 50 μl of the secondary antibodies. The anti-rabbit 488 secondary antibody was used for the collagen I, collagen IV, elastin, fibronectin, and laminin samples. The anti-mouse 594 secondary antibody was used for the hyaluronic acid (HA) sample. After 1 hour of incubation at 4° C., the samples were again rinsed three times with 1 ml PBS to remove unbound secondary antibodies. The coverslips were mounted to slides (7.5 cm long×2.5 cm wide) using Slowfade Diamond Antifade Mountant (Fisher Scientific). Slides were examined using a confocal laser scanning microscope (Ti-E A1rSi System, Nikon Instruments, Inc. Melville, NY, USA) at 20× mag. Secondary only controls (sections stained only with the secondary antibodies) were used to adjust brightness and intensity to account for any background fluorescence due to non-specific antibody absorption on to samples. Brightness and intensity settings were kept uniform so that images from all groups could be compared. Samples were imaged using optical sectioning. For the optical sectioning, between 35-55 slices or planes of focus were collected starting at the surface and moving into the sample at approximately 0.51 μm intervals. The collected images were stacked to create composite image. There were n=3 images collected for each extracellular matrix component evaluated.

The sterilized porcine placental membranes showed positive staining for each of collagen I, collagen IV, elastin, laminin, fibronectin, and hyaluronic acid (HA). Collagen I and collagen IV showed the highest intensity of staining, although all antibodies did show positive staining. Based on the immunostaining, the porcine placental membranes contained collagen I, collagen IV, elastin, laminin, fibronectin, and hyaluronic acid (HA).

We claim:

1. A method of treating a wound, the method comprising the step of:

introducing a birth tissue composition on or around the wound, wherein the birth tissue composition comprises a dehydrated, decellularized porcine placental membrane that is prepared by a method comprising:

(i) a bioburden reduction step comprising contacting unprocessed porcine placental membrane with a 3M sodium chloride solution at about 20 mL per gram of porcine placental membrane for about 30 minutes to about 2 hours to reduce microbial load and form a bioburden reduced porcine placental membrane;

(ii) decanting the sodium chloride solution;

(iii) rinsing the sodium chloride solution from the bioburden reduced porcine placental membrane with water;

(iv) a detergent rinse step comprising contacting the bioburden reduced porcine placental membrane after step (iii) with a detergent solution comprising at least one anionic detergent and at least one protease enzyme, wherein the anionic detergent is present at a concentration of about 0.25% to about 3% w/v, wherein the contacting occurs for about one hour to about three hours, for removal of cellular debris while preserving extracellular matrix integrity; and (v) decanting the detergent solution to form a detergent rinsed porcine placental membrane;

(vi) rinsing the detergent solution from the detergent rinsed porcine placental membrane with water;

(vii) a viral inactivation step comprising immersing the rinsed porcine placental membrane after step (vi) in a sodium hydroxide solution at a concentration of about 0.25M for about 15 minutes to about 45 minutes to form a viral inactivated porcine placental membrane;

(viii) rinsing the sodium hydroxide solution from the viral inactivated porcine placental membrane with water;

(ix) introducing from about 5 mL to about 50 mL of buffer solution per gram of porcine placental membrane to the rinsed porcine placental membrane after step (viii);

(x) decanting the buffer solution;

(xi) measuring the pH of the porcine placental membrane after step (x);

(xii) repeating steps (ix)-(xi) until the pH of the porcine placental membrane is between about 6.8 and about 7.2;

(xiii) rinsing the buffer solution from the porcine placental membrane after step (xii) with water; and (xiv) dehydrating the porcine placental membrane after (xiii) to form the dehydrated, decellularized porcine placental membrane, wherein the dehydrated, decellularized porcine placental membrane exhibits a final pH of between about 6.8 and about 7.2, and wherein the dehydrated, decellularized porcine placental membrane retains collagen I, collagen IV, elastin, laminin, fibronectin, and hyaluronic acid.

2. The method of claim 1, wherein the wound is selected from the group consisting of a burn, cut, abrasion, and ulcer.

3. The method of claim 1, wherein the wound is a partial-thickness wound, full-thickness wound, pressure ulcer, venous ulcer, diabetic ulcer, chronic vascular ulcer, tunneled/undermined wound, surgical wound, trauma wound, or draining wound.

4. The method of claim 3, wherein the wound is located anywhere in or on a mammalian body.

5. The method of claim 1, wherein the birth tissue composition is held in place by one or more sutures or staples.

6. The method of claim 1, further comprising the step of hydrating the birth tissue composition after introduction to the wound.

7. The method of claim 1, wherein the birth tissue composition further comprises at least one antibiotic, anti-inflammatory agent, growth factor, or a combination thereof.

8. The method of claim 1, wherein the birth tissue composition is combined with a substrate.

9. The method of claim 8, wherein the substrate comprises at least one sterile gauze, sterile polymer material, biomaterial, or a combination thereof.

10. The method of claim 1, wherein the birth tissue composition is held in place by musculature or skin.

11. The method of claim 1, wherein the birth tissue composition is placed over an implant or device.

12. The method of claim 1, wherein the birth tissue composition covers an implant or other device placed on or within a mammalian body.

13. The method of claim 1, wherein step (i) is performed for about one hour.

14. The method of claim 1, wherein in step (iv) the detergent solution comprises sodium linear alkylaryl sulfonate, phosphates, carbonates, and at least one protease enzyme.

15. The method of claim 1, wherein in step (iv) the anionic detergent is present at a concentration of about 1% w/v.

16. The method of claim 1, wherein step (vii) is performed for about 20 minutes.

17. The method of claim 1, wherein in step (ix) the buffer solution is phosphate-buffered saline.

18. The method of claim 1, wherein step (xiv) comprises contacting the porcine placental membrane with 200 proof ethanol.

* * * * *